United States Patent [19]

Jaeger

[11] Patent Number: 4,844,814
[45] Date of Patent: Jul. 4, 1989

[54] SYSTEM AND METHOD FOR SEPARATING SOLUTES AND PARTICULATES IN SOLVENTS BY ENHANCED DIFFUSION PRODUCED BY TUNED OSCILLATIONS

[75] Inventor: Marc J. Jaeger, Gainesville, Fla.

[73] Assignee: University of Florida, Gainesville, Fla.

[21] Appl. No.: 152,358

[22] Filed: Feb. 4, 1988

[51] Int. Cl.$^4$ .............................................. B01D 43/00
[52] U.S. Cl. ............................... 210/748; 204/157.42; 204/157.62
[58] Field of Search ............... 210/638, 637, 650, 653, 210/748, 695, 388; 128/653; 204/180, 186, 149, 151, 157.15, 157.42, 157.62

[56] References Cited

U.S. PATENT DOCUMENTS

| 4,161,013 | 7/1979 | Gropzinsky et al. | 210/650 |
| 4,307,726 | 12/1981 | Paulson et al. | 128/653 |
| 4,361,484 | 11/1982 | Larsson et al. | 210/637 |
| 4,717,480 | 1/1988 | Akedo et al. | 210/638 |

Primary Examiner—Frank Sever
Attorney, Agent, or Firm—Dennis P. Clarke

[57] ABSTRACT

The present invention is predicated on the discovery that mixtures of solutes and/or particulates of differing masses dissolved or suspended in a liquid media can be separated at high differential flow rates by an enhanced diffusion technique involving the oscillation of the liquid media containing the solutes and/or particulates within one or more ducts or capillaries in the presence of axial concentration gradients.

13 Claims, 5 Drawing Sheets

SYSTEM AND METHOD FOR SEPARATING SOLUTES AND PARTICULATES IN SOLVENTS BY ENHANCED DIFFUSION PRODUCED BY TUNED OSCILLATIONS

BACKGROUND OF INVENTION

1. Related Applications

The invention described herein is related to that described in U.S. patent application Ser. No. 002,268, filed Jan. 12, 1987.

2. Field of the Invention

The present invention relates to a system and method for separating solutes dissolved in and particulates suspended in liquid solvents by diffusion using tuned oscillations.

3. Prior Art

Diffusion has long been employed to separate molecules. Graham [On the law of diffusion of gases. Philosophical Mazagine, Vol. 2, pp. 175–351 (1833)], who first related the molecular diffusion coefficient to the square root of molecular weight, separated gases based upon this principle in the 19th century. Hertz developed a technique based on diffusion to separate gases in a countercurrent system [Z. Physik., Vol. 19, p. 35 (1923); Z. Physik, Vol. 91, p. 810 (1934)].

This technique was extended to liquids by Lange [Z. Naturwiss., Vol. 16, p. 115 (1928); Vol. 17, p. 228 (1928)]. There is evidence that students of Lange expanded on this work and reported their results in papers published in East Germany that are not readily available. East German Patent No. 54339 describes the method of Lange as one involving the enhancement of the diffusion rate by oscillations and regeneration of the solvent by successive distillation and condensation.

Dreyer et al [Die Steigerung des Diffusionstransportes durch Pulsationsdiffusion, Z. Naturforsch. Vol. 23, pp. 498–503 (1968); Die Bestimmung von Diffusionskoeffizienten nach der Pulsationsmethode, Z. Naturforsch. Vol. 24, pp. 883–886 (1969)] describe a system for determining the diffusion coefficients of solutes such as KC, NaCl and $CaCl_2$ comprising two containers connected by a capillary and a mechanism for creating pulsating oscillations in the liquid contained in the capillary. Although the authors discovered an enhancement of transport by several orders of magnitude across the capillary, they do not describe or suggest utilization of the system to separate solutes contained in a common solvent.

Modified principles of diffusion are used industrially today, especially to separate isotopes of uranium. Diffusion has been used to separate solutes in liquid solution, however, the efficacy of the process is low because the molecular diffusion coefficient of solutes in liquids is about five orders of magnitude smaller than the diffusion coefficient of gases in a gaseous phase, thus reducing the possible yield for a given configuration.

Enhanced diffusion (or dispersion) by oscillatory motion of a fluid finds its roots in the theoretical work by Watson (J. Fluid Mech., 133, p. 233, (1983) who himself expanded on a study by Taylor on the dispersion of solutes in steady laminar flow (Proc. R. Soc. London Ser. A 219, p. 186 (1953). Kurzweg et al recently described the conditions of optimal transport in gases by proper tuning of the experimental variables (Phys. Fluids, Vol. 29, p. 1324 (1986)).

The general principal involved may be described thusly: The oscillation of a fluid column in a tube generates a large surface between the oscillating core and the boundary layer which is essentially not moving. This surface is made available for diffusion. The theory predicts that, under certain conditions, the dispersion coefficient (i.e., the effective diffusion coefficient) is proportional to the square root of oscillation frequency, to the square of the average oscillation amplitude, and to the molecular diffusion coefficient. The diffusion rate (flux) of a solute in an oscillatory system is proportional to the dispersion coefficient, and to the concentration gradient and is dependent on geometry.

It is an object of the present invention to provide a differential diffusion system and method for separating solutes and/or particulates dissolved or suspended in liquid media.

SUMMARY OF THE INVENTION

The foregoing and other objects are realized by the present invention, one embodiment of which is a system for separating solutes of different masses from each other and/or solutes of different masses from particulates of different sizes by enhanced diffusion comprising at least one separating device comprising:

a pair of liquid reservoirs;

at least one duct connecting the liquid reservoirs; and means for establishing oscillatory axial movement of liquid within the at least one duct.

A further embodiment of the invention comprises a method for separating solutes or particulates of differing masses from a mixture thereof contained in a liquid and from each other by enhanced diffusion comprising conducting at least one cycle of:

feeding a liquid containing a member selected from the group consisting of a mixture of the solutes of different masses to be separated or a mixture of at least one solute and at least one particulate of different masses to be separated, into a first reservoir which is connected by at least one duct to a second reservoir;

feeding into the second reservoir or liquid capable of receiving and containing the solutes or particulates;

establishing oscillatory axial movement of liquid within the at least one duct whereby the liquid in the second reservoir is enriched in the heavier of the member mixture components.

DETAILED DESCRIPTION OF THE INVENTION

The present invention is predicated on the discovery that mixtures of solutes and/or particulates of differing masses dissolved or suspended in a liquid media can be separated at high differential flow rates by an enhanced diffusion technique involving the oscillation of the liquid media containing the solutes and/or particulates within one or more ducts or capillaries in the presence of axial concentration gradients.

Figure 1:
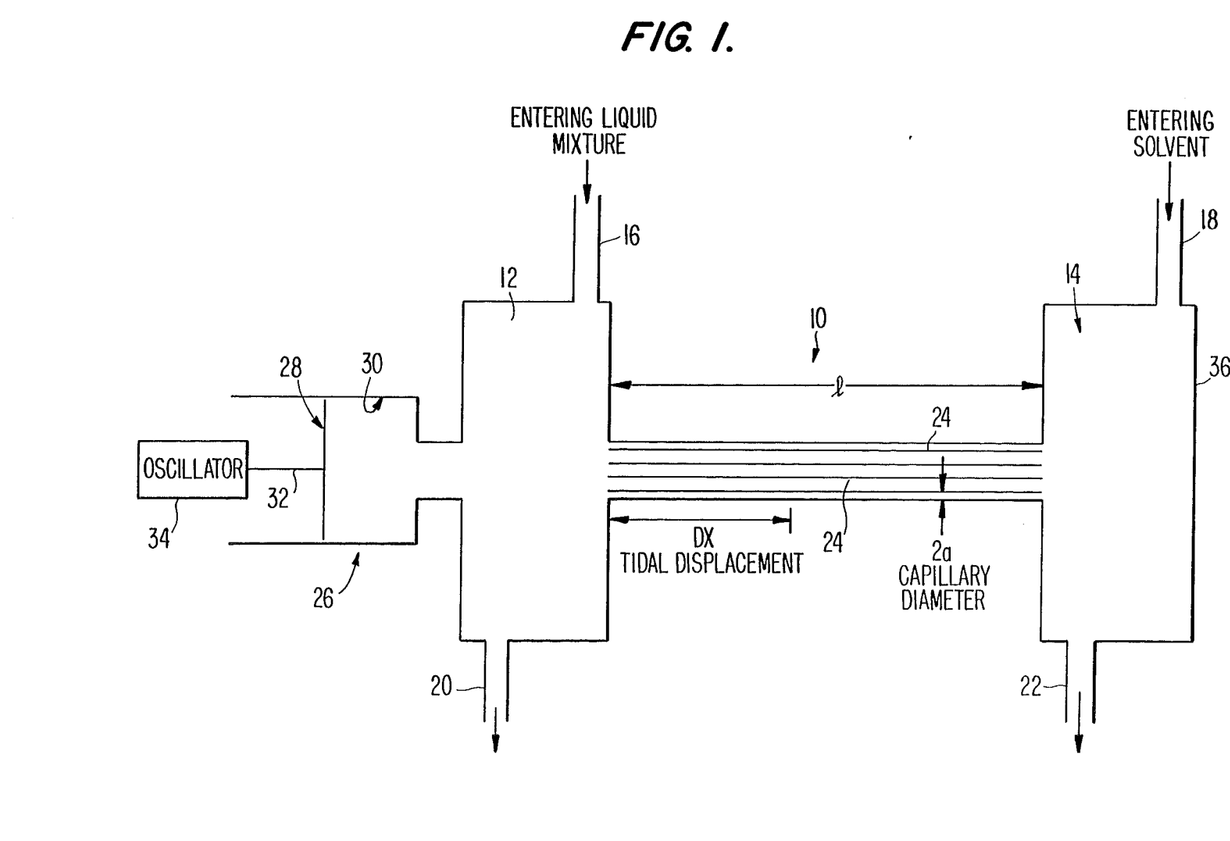
FIG. 1 is a diagrammatical sectional view of an embodiment of a diffusion separating system according to the invention.

Referring to FIG. 1, a separation device 10 in accordance with the invention includes a pair of liquid reservoirs 12 and 14, equipped with liquid inlets 16 and 18, respectively, and liquid outlets 20 and 22, respectively.

The two reservoirs 12 and 14 are connected by at least one, and preferably a plurality, of ducts 24. The ducts 24 preferably have a diameter of from about 0.1 to about 0.2 cm.

The reservoirs 12 and 14 and the ducts 24 are adapted to receive and hold and transfer the liquid media, respectively.

Acting on the liquid media between the reservoirs 12 and 14, in this example, within reservoir 12 is an oscillatory displacement device 26. As a representative example, the oscillatory displacement device 26 comprises a driving piston 28 reciprocating within a cylindrical bore 30 in direct communication with the reservoir 12 and driven via a shaft 32 by an external mechanical oscillator 34. Typically, the driving piston 28 oscillates sinusoidally, however, any suitable oscillation wave form may be used.

Since the liquid is substantially incompressible, in order to keep the system entirely filled at all times with no voids or dilutions of the mixture, a displacement accommodating device 36 is connected to reservoir 14. In the example shown, the displacement accommodating device comprises what may be viewed as a passive resilient member, preferably a membrane.

With this arrangement, as the piston 28 oscillates, liquid moves alternatively axially in opposite directions within the ducts 24. The displacement accommodating member 36, due to its resilient nature, returns energy to the driving piston 28. The oscillation amplitude is selected such that the extent of liquid movement (tidal displacement DX) within the ducts 24 is less than one-half of the length of the ducts.

The feeding and withdrawal rates through inlets 16 and 18 and outlets 20 and 22 are adjusted so as to be substantially equal to ensure that there is no net convection flowing along the diffusion cells.

Figure 2:
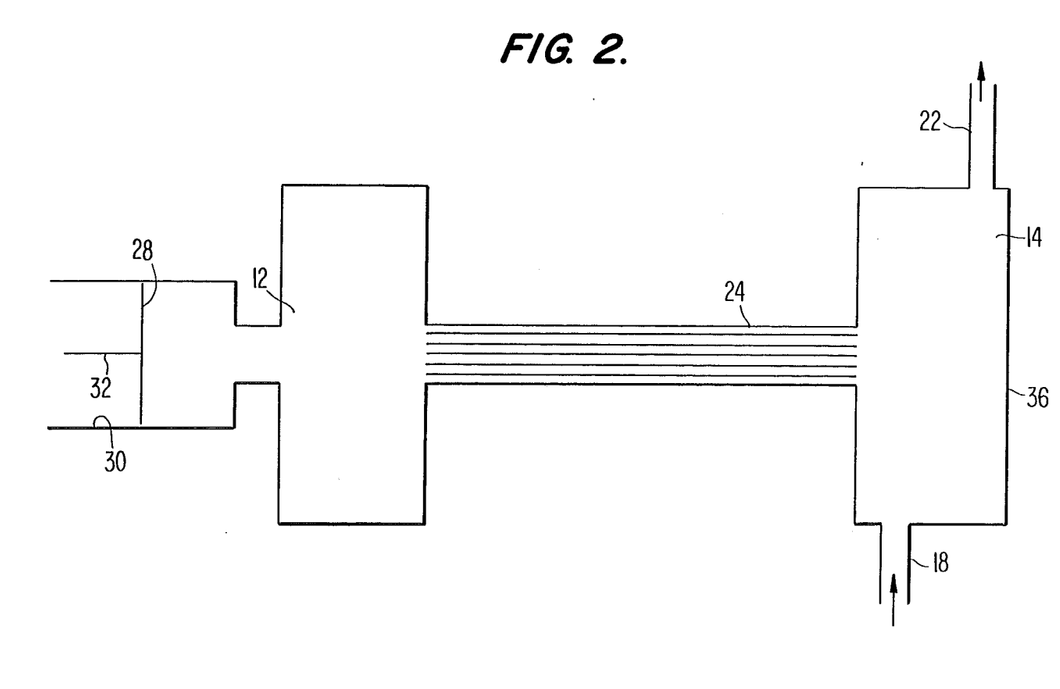
FIG. 2 is a diagrammatical sectional view of a further embodiment of the system according to the invention.

Referring to FIG. 2, reservoir 12 is filled with the media containing the solutes or particulates to be separated while reservoir 14 is filled with the solvent and continuously flushed with the solvent through inlet 10 and outlet 22. Solutes or particulates are transported at different rates according to size or mass by enhanced diffusion down the concentration gradient to reservoir 14.

Figure 3:
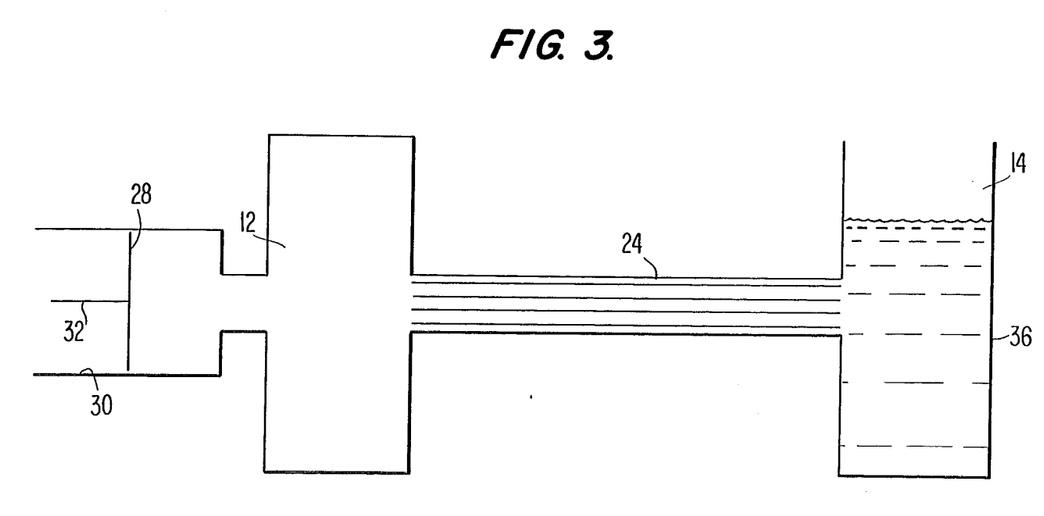
FIG. 3 is a diagrammatical sectional view of a further embodiment of the system according to the invention.

Referring to FIG. 3, the system is identical to that in FIG. 2, except that reservoir 14 is not provided with inlet and outlet means and is not continuously flushed with carrier liquid.

Figure 4:
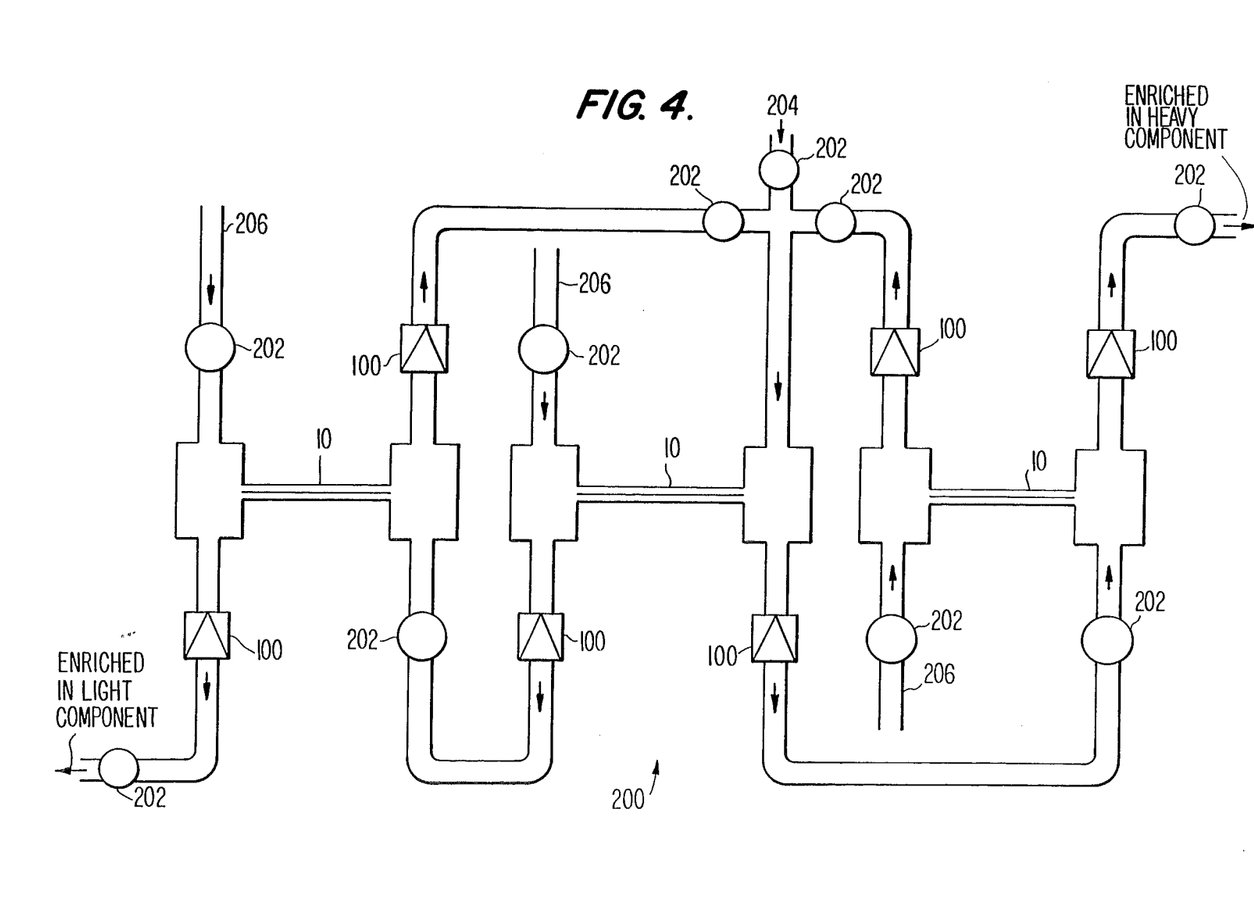
FIG. 4 is a diagrammatical sectional view of a cascade system embodiment of the invention.

Referring to FIG. 4, a standard Hertz cascade cycle 200 is shown which can be used to produce an essentially complete separation of the components of a mixture. The cycle consists of three basic elements: diffusion tubes 10, concentration columns 100 and pumps 202. The mixture to be separated enters the system via injection port 204. Solvent enters via ports 206. In the system shown the light solute or particulate component diffuses faster down the diffusion cells 10 from right to left than does the heavier component. As a result the mixture exiting the left of each diffusion cell is enriched with the lighter species, while the mixture exiting the right side of the diffusion cell is enriched with the heavier molecules. The function of the concentration column is to remove solvent periodically; while the pumps insure substantially equal feeding and withdrawing rates to ensure that there is no net convection flowing along the diffusion cells and that enriched mixtures are moved to the next stage.

Figure 5:
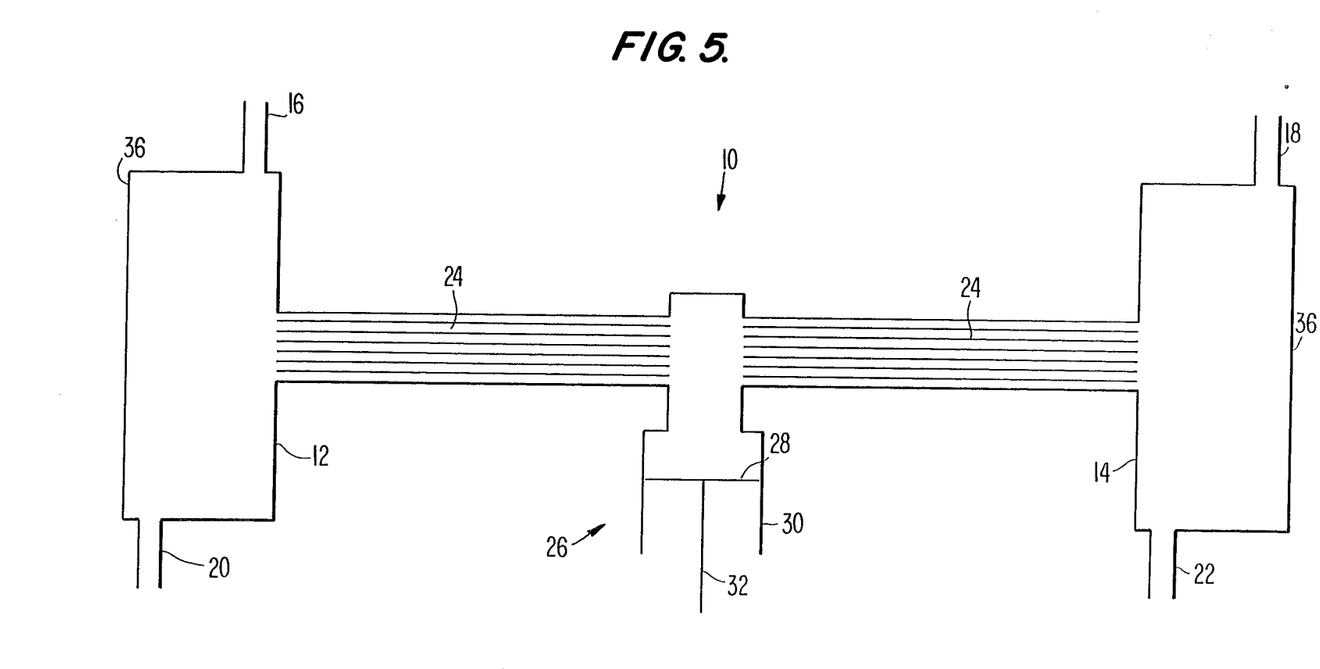
FIG. 5 is a diagrammatical sectional view showing an alternative location of the pump mechanism.

Referring to FIG. 5, the system depicted differs from that shown in FIG. 1 in that oscillatory displacement device 26 is positioned between reservoirs 12 and 14.

It will be understood that any of the many conventional and well-known methods of concentration such as distillation or centrifugation may be employed in the practice of the invention depending, of course, upon the nature of the liquid media employed and the solutes and/or particulates to be separated.

It is believed that the principles, operation and exemplary embodiments of the invention will all be understood from the foregoing. Following is a detailed description of an embodiment of a method of the invention.

The device preferably consists of a diffusion tube of specified dimensions in which oscillations are generated which have a specified frequency and amplitude. Optimal oscillation frequency and amplitude depend on the tube's geometry. The diffusion tube is connected on either side to a container (FIGS. 1–3). One container holds the solution of solutes and/or particulates to be separated, the other the liquid media or solvent. The dimension of the containers is not critical, however, the geometry of the diffusion tube is quite critical. A pump preferably generates the oscillatory motions. This pump may be conveniently connected to either of the two containers. It may also be located in the middle of the diffusion tube as shown in FIG. 5. In that case the diffusion tube is divided by the pump into two sections wherein the oscillatory motions in the two sections are opposite. Specifically, dimensions of the diffusion tube and the operating conditions should be close to the following:

Preferably, a diffusion tube comprising a bundle of capillaries of 1 to 2 mm ID and 120 cm length is used. The oscillation amplitude is between 20 and 40 cm (=stroke volume of pump divided by overall cross-sectional area of the capillaries) and the frequency is 20 rpm. These conditions provide for the Reynolds number to be less than 2000 establishing, presumably, laminar flow and for the Wormersley number to be around unity. The Reynolds number is equal to the product of capillary diameter times oscillation amplitude time frequency (in cycles per second) divided by the kinematic viscosity. The Wormersley number is equal to the radius times the square root of the product of two times $\pi$ times frequency divided by the kinematic viscosity. These conditions also guarantee that fluid mechanical resistance will not be overly high. The boundary layer thickness is, with these conditions, not much greater than the mean diffusion distance which a molecule may travel due to molecular diffusion during one-half period. An oscillation amplitude of less than one-half of the length the diffusion tube is preferably used, thus avoiding bulk transport while maximizing diffusional transport. Using cuprisulfate, an effective diffusion coefficient of 1.7 cm$^2$/sec (N=13) was measured, a value close to the theoretically expected value of 1.2 cm$^2$/sec. The molecular diffusion coefficient of cuprisulfate is 0.00007 cm$^2$/sec.

Variations of the diffusion parameters include the increase of oscillation amplitude to 40 or 50% of the length of the diffusion tube, increase of the length of the diffusion tube itself, and reduction of the capillary radius. Very small capillaries or beads were not employed for fear of effects of adsorption. If diffusion parameters are varied it is important to maintain the Reynolds and the Wormersley number within the constraints mentioned above.

The variable that is most easy to modify is the number of capillaries, i.e., the total cross-sectional area. The rate of solute transport and the rate of separation are directly proportional to this area. A diffusion rate was achieved with glucose averaging 5 mg/min for a concentration in reservoir 12 (FIG. 1) of 467 mg/100 ml. The total cross-section of all capillaries was 0.22 cm$^2$. The rate could have, obviously, been increased by raising the total cross-section.

Secondary parts of the device include the pump and the two containers on either side of the diffusion tube. For best mixing a container size of at least 10 times larger than the total volume of the capillaries should be used. In one embodiment the pump is connected to one container and the second container is used as a recipient for the solvent and as an expansion chamber that allows for the volume changes generated by the pump. Small changes in the configuration of the two containers allow for three different uses of the device each of which has its own advantage.

The invention is illustrated by the following non-limiting examples.

EXAMPLE 1

Referring to FIG. 2, container 12 is filled with the solutes to be separated while container 14 (the expansion chamber) is continuously flushed with solvent. Solutes in container 12 are transported by enhanced diffusion down the concentration gradient to container 14. It was found, with all variables except molecular size being the same, a washout time constant for glucose of 179 min (N=5), for methylene blue of 308 min, (N=22) for cuprisulfate 168 min (N=13), and for blue Dextran (MW 2,000,000) of 1597 min (N=4). For red blood cells the time constant was found to be so long that it could not be measured accurately with the available techiques (N=4). Compared to that of smaller solutes, the time constant for red blood cells was nearly infinite. The difference between time constants allows one to purify molecules and particulates of different size. With standard analytical techniques one can predict that using in container 12 a mixture of dextran and glucose, the concentration of glucose will reach 1% of initial after 4.6 time constants (or 828 min) in container 12 while the dextran concentration in container 12 will drop only to 60% of initial; corresponding to a 60:1 purification.

EXAMPLE 2

Referring to FIG. 3, container 14 is not flushed. It is filled at the beginning with solvent. Solutes diffuse from container 12 into container 14 until equilibrium is reached. The equilibration follows an exponential time course. Unequal diffusion rates result, however, in a transient enrichment of container 12 in the large component and of container 14 in the small component. Maximal separation is obtained at time $t = (\ln(T_H T_L))/(1/T_L - 1/T_H)$ when $T_H$ is the time constant for the heavy component and $T_L$ the time constant for the light component. The device of FIG. 3 is convenient for measuring T and for determining the effective diffusion coefficient. It does not result in any loss of substance.

EXAMPLE 3

Referring to FIG. 1, both containers are perfused with a low perfusion rate designed to maintain a steady state concentration gradient between them. Container 12 is perfused with the liquid containing solutes wherein container 14 is perfused with solvent. A concentration gradient of 10:1 is preferred. Thus, if the concentration of the lighter solute in container 12 is 100 the concentration of the solute in container 14 should be adjusted to 10. This ratio provides for excellent yield as well as good separation. This configuration is a steady state process suitable for continuous use as required by technical or industrial operations.

EXAMPLE 4

Referring to FIG. 4, a diagram of a cascade of separating units is shown. Such cascades are standard in industry. Cascades other than the one shown, use the countercurrent principle for higher efficiency and lower dilution. Each stage of a cascade may best be controlled as in Example 3.

The method and system of the invention has particular suitability for biochemists, both in research and in industry, since they produce high yields and do not require constant replacement of parts. The invention depends on molecular mobility, which itself depends on molecular size and other factors. It may be used to measure mobility to study molecular interactions. The system is technically simple and requires a low energy input. Any solvent may be used that dissolves the solvent or suspends the particulates.

The method and system of the invention device separate molecules dissolved in a liquid solvent based on their different molecular diffusion rate, i.e., on their different size. Since molecular sizes of organic and inorganic molecules vary greatly, the power of separation is potentially great. The device also separates suspended particulates from dissolved molecules. The device enhances the diffusional transport of molecules by five to six orders of magnitude, a fact that results in a yield (i.e., rate of substance separated) which is highly attractive. The device generates linear concentration gradients for each of the solutes involved. The device separates physically the mixed solutes and the partially separated solutes by a large distance (feet). In earlier devices the solution and the solvent were separated by distances measured only in micrometers. The device is simple to construct and the process is gentle to the molecules thereby preventing breakdown thereof.

It will be understood that the method and system of the invention are adapted for separating solutes from solutes, particulates from particulates and solutes from particulates.

I claim:

1. A method for separating solutes or particulates of differing masses from a mixture thereof contained in a liquid and from each other by enhanced diffusion comprising conducting at least one cycle of:
    feeding a liquid containing a member selected from the group consisting of a mixture of said solutes of differing masses to be separated, a mixture of particulates of differing masses to be separated, a mixture of particulates of differing masses to be separated, or a mixture of at least one solute and at least one particulate of differing masses to be separated into a first reservoir which is connected by at least one duct to a second reservoir;

feeding into said second reservoir a liquid capable of receiving and containing said solutes or particulates;

establishing sinusoidal oscillatory axial movement of liquid within said at least one duct such that the tidal displacement in said at least one duct is maintained sufficiently small so as to maintain a condition of zero net convection between the ends of said at least one duct and the liquid in said second reservoir is enriched in the heavier of said member mixture components.

2. A method according to claim 1 wherein said reservoirs are connected by as plurality of ducts.

3. A method according to claim 1 including withdrawing from said second reservoir a liquid containing said member enriched in the lighter of said mixture components.

4. A method according to claim 3 including withdrawing from said first reservoir a liquid containing said member enriched in the heavier of said mixture components.

5. A method according to claims 3 or 4 comprising separating at least a portion of solute or particulate from said withdrawn liquid mixture.

6. A method according to claim 5 wherein said solute or particulate is removed by concentration.

7. A method according to claim 3 including feeding into said second reservoir said liquid capable of receiving and containing said solutes or particulates.

8. A method according to claim 7 including feeding into said first reservoir said liquid containing said member.

9. A method according to claim 8 including maintaining feeding and withdrawing rates into and out of said reservoirs substantially equal such that a solute or particulate concentration gradient is maintained between the liquids in said reservoirs.

10. A method according to claims 7 or 8 comprising conducting multiple said cycles in cascade fashion wherein at least one of said liquids containing a member enriched in one of said heavier or lighter mixture components thereof withdrawn from a reservoir in a previous cycle is fed into a reservoir in a subsequent cycle whereby such succeeding withdrawn liquid is more enriched in said lighter or heavier mixture component than the previously withdrawn liquid.

11. A method according to claim 10 wherein at least a portion of said solute or particulate is separated from at least one of said withdrawn liquid mixture.

12. A method according to claim 11 wherein said solute or particulates are removed by concentration.

13. A method according to claim 12 wherein said liquid is alternately moved axially in opposite directions within said at least one duct, that extent of movement therewithin being less than the length thereof.

* * * * *

UNITED STATES PATENT AND TRADEMARK OFFICE
CERTIFICATE OF CORRECTION

PATENT NO. : 4,844,814
DATED : July 4, 1989
INVENTOR(S) : MARC J. JAEGER

It is certified that error appears in the above-identified patent and that said Letters Patent is hereby corrected as shown below:

In column 7, Claim 2, line 2, correct "as" to read --a--.

Signed and Sealed this

Thirteenth Day of March, 1990

Attest:

JEFFREY M. SAMUELS

*Attesting Officer*          *Acting Commissioner of Patents and Trademarks*